(12) United States Patent
Bock et al.

(10) Patent No.: US 6,869,948 B1
(45) Date of Patent: Mar. 22, 2005

(54) MELOXICAM FOR ORAL ADMINISTRATION

(75) Inventors: Thomas Bock, Biberach (DE); Paul Saegmueller, Bergatreute (DE); Peter Sieger, Mittelbiberach (DE); Dietrich Tuerck, Ulm (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 554 days.

(21) Appl. No.: 09/277,049

(22) Filed: Mar. 26, 1999

Related U.S. Application Data

(60) Provisional application No. 60/088,850, filed on Jun. 10, 1998.

(30) Foreign Application Priority Data

Mar. 27, 1998 (EP) .............................. 98105569

(51) Int. Cl.⁷ ..................... A61K 31/54; C07D 279/16
(52) U.S. Cl. ...................... 514/226.5; 544/49
(58) Field of Search .......................... 544/49; 514/226.5

(56) References Cited

U.S. PATENT DOCUMENTS

| 4,233,299 A | 11/1980 | Trummlitz et al. |
| 4,748,174 A | 5/1988 | Veronesi |

FOREIGN PATENT DOCUMENTS

| DE | 37 00 172 A | 7/1987 |
| EP | 0 002 482 A | 6/1979 |
| WO | WO 97 17978 A | 5/1997 |
| WO | WO 99 09988 A | 3/1999 |

OTHER PUBLICATIONS

Luger et al; "Structure and physicochemical properties of meloxicam, a new NSAID"; European Journal of Pharmaceutical Sciences; Bd. 4, 1996, Seiten 175–187, XP002074736 *siehe Zusammenfassung; Seite 177, linke Spalte; und Seite 178 Tabelle 1*.

Primary Examiner—Richard L. Raymond
Assistant Examiner—Tamthom N. Truong
(74) Attorney, Agent, or Firm—Robert P. Raymond; Timothy X. Witkowski; Anthony P. Bottino

(57) ABSTRACT

The invention relates in its first aspect to a rapidly decomposing tablet for pain therapy containing meloxicam [4-hydroxy-2-methyl-N-(5-methyl-2-thiazolyl)-2H-1,2-benzothiazine-3-carboxamide-1,1-dioxide] in the form of a salt with an inorganic or organic base providing rapid absorption of the active substance, the process of its preparation by direct tabletting, and furthermore relates in a second aspect to the crystalline meloxicam meglumin salt mono- and dihydrate and the preparation thereof.

18 Claims, 9 Drawing Sheets

MELOXICAM FOR ORAL ADMINISTRATION

RELATED APPLICATIONS

Figure 1:
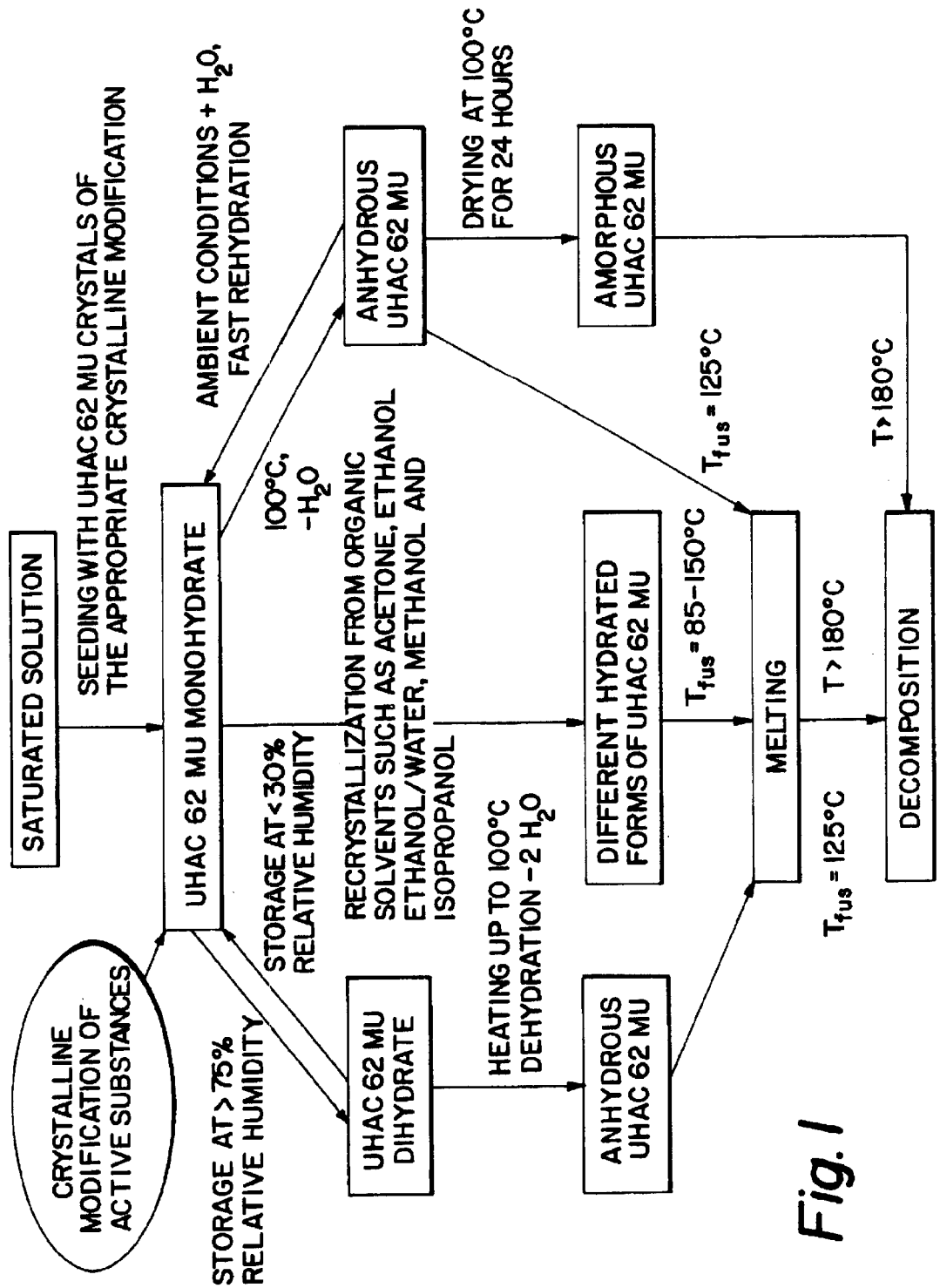

The benefit of prior provisional application Ser. No. 60/088,850, filed on Jun. 10, 1998, is hereby claimed.

TECHNICAL FIELD OF THE INVENTION

The invention relates to new pharmaceutical compositions for the oral administration of the NSAID (nonsteroidal-anti-inflammatory drug) meloxicam.

BACKGROUND OF THE INVENTION

The drugs used for the treatment of rheumatic diseases often have antiphlogistic as well as analgesic properties. For this reason they are used not only to treat chronic rheumatic diseases but also for acute rheumatic attacks and for acute pain treatment.

Many of these pharmaceutical compositions have only limited solubility and for this reason are absorbed only slowly by the body. In the treatment of acute pain, a rapid influx of active substance is essential to ensure that the activity sets in rapidly. It is therefore often necessary to increase the speed of dissolution and solubility of the active substances in question.

For known drugs in this field, different approaches have been adopted, e.g. ibuprofen and diclofenac are used in the form of their salts or piroxicam is used in the form of β-cyclodextrin inclusion compounds. However, when administered by oral route, these active substances do not always exhibit a sufficient plasma concentration for rapid effect within a short time. The pharmacokinetic differences of ibuprofen-lysinate compared with ibuprofenic acid are described for example in Int. J. Clin. Pharmacol., Ther. Toxicol. ,Vol. 27, No. 7, 324–328 (1989). It says that the average peak-plasma level measured on 8 fasting test subjects in the case of ibuprofen-lysinate (1000 mg, film-coated tablet) was achieved on average 0.55 h after administration and was 69.1: g/ml, whereas the corresponding values for ibuprofenic acid (600 mg, sugar-coated tablet) are given as 0.89 h and 50.8: g/ml. In non-fasting test subjects the differences lose statistical significance according to the authors and amount to 50.3: g/ml ibuprofen-lysinate after 1.18 h and 44.6 g/ml for ibuprofenic acid after 1.55 h. DE 37 00 172 explains that numerous NSAID's do not dissolve easily in water and are therefore not really suitable for preparing parenteral formulations. To overcome this problem, the use of N-(methyl)-glucamine and glucamine salts of a number of NSAIDs, including, inter alia, Isoxicam, Tenoxicam and Piroxicam has been proposed. A parenteral Piroxicam-N-(methyl)-glucamine formulation is described as Example 4. It is also stated that these salts can also be administered in oral, rectal or topical formulations, but the published application contains no information on the absorption of oral formulations. The problem described therein, namely the preparation of a parenteral aqueous formulation of a comparatively insoluble active substance, differs substantially from the objective of the present invention. As explained hereinafter, this consists in providing an orally administered solid pharmaceutical preparation of meloxicam which produces effective plasma levels soon after administration. In addition, the starting point of the present invention was considerably more difficult, as free meloxicam is less water-soluble, by a factor of about 10, than free piroxicam over a wide pH range (European Journal of Pharmaceutical Science 4 (1996), 175–187, particularly FIG. 10 on page 184).

Meloxicam (4-hydroxy-2-methyl-N-(5-methyl-2-thiazolyl)-2H-1,2-benzothiazine-3-carboxamide-1,1-dioxide) is an antirheumatic which is distinguished by the fact that it is well tolerated by the stomach at the doses necessary for therapy. The active substance and its sodium salt—as well as its N-methyl-D-glucamine salt (meglumin salt) are described in EP-A-0 002 482. The anti-inflammatory and pain-relieving properties of meloxicam also make this active substance very interesting for use in pain therapy. However, the active substance has very low solubility in the acid range which prevails in the upper part of the gastrointestinal channel. It is therefore absorbed with a time delay after administration. Maximum plasma levels are reached within 2–8 hours, depending on the formulation. However, the activity is long-lasting and highly effective. As a rule, therefore, a single dose each day is sufficient. In order to open up this active substance, which is suitable for pain therapy, for treating acute conditions as well, it is necessary to ensure rapid absorption and, at the same time, a rapid onset of activity.

DESCRIPTION OF THE INVENTION

The object of the present invention is to provide a solid pharmaceutical preparation of meloxicam, suitable for oral administration, from which the active substance is released and absorbed rapidly, so that a plasma level suitable for treating acute pain can be achieved sufficiently rapidly. The following profile of requirements can be defined in connection with this.

The maximum plasma level $C_{max}$ should be higher than after the administration of an equal dose of a conventional meloxicam capsule formulation and should be achieved very much sooner. A high enough effective plasma level should then be maintained for a certain length of time. In particular, $C_{max}$ should be reached at the latest two hours after the administration of a single dose and should be at a dosage of 7.5 mg in the range from 650 to 1000 ng/ml. Ideally $C_{max}$ at this dosage should correspond to about twice the maximum plasma level which is achieved with the conventional 7.5 mg capsule formulation and should therefore be in the range from 800 to 900 ng/mL. After the maximum plasma level is exceeded, a plasma level of 500 to 700 ng/ml should be maintained for 1 to 3 hours, but ideally a plasma level of 550 to 650 ng/ml, which corresponds to the steady state average plasma levels of about 600 ng/ml after the administration of the conventional 7.5 mg capsules. Moreover, the total absorption of the formulation according to the invention and the conventional capsule formulation with the same dose should be equivalent.

Meloxicam is capable of forming salts with inorganic bases, e.g. the sodium, potassium or ammonium salt, and also with organic bases, e.g. the meglumin salt, the Tris salt (Tris-(hydroxymethyl)aminomethane) or salts with basic amino acids such as L-lysine or L-arginine. In connection with the objective of the invention the solubilities of the active substance and its salts are of interest.

TABLE 1

Saturation solubility of meloxicam and its salts in various dissolving media

| Medium | Solubility at ambient temperature [mg/100 ml] | | | |
|---|---|---|---|---|
| | Meloxicam | Sodium salt | ammonium salt | meglumin salt |
| 0.1 N hydrochloric acid (pH 1) | 0.09 | 0.05 | 0.04 | 0.1 |
| Buffer pH 4 | 0.05 | 0.02 | 0.02 | 0.04 |
| Water (pH 7) | 0.2 | 785 | 230 | 860 |
| Buffer pH 7.4 | About 100 | 635 | 285 | 1290 |

TABLE 1-continued

Saturation solubility of meloxicam and
its salts in various dissolving media

| Medium | Solubility at ambient temperature [mg/100 ml] | | | |
|---|---|---|---|---|
| | Melox-icam | Sodium salt | ammonium salt | meglumin salt |
| Buffer pH 10 | 231 | 1215 | 440 | 2315 |
| 0.1 N sodium hydroxide solution (pH 13) | 2570 | 1215 | 1960 | 2900 |

The data in Table 1 show the following:

Both meloxicam and meloxicam salts are only poorly soluble in aqueous systems at pH values $\leq 4$, with no apparent significant differences in the solubility of the different compounds. As the pH increases to between 4 and 10 the solubility of the meloxicam salts increases, particularly the sodium and meglumin salt, significantly more than that of the free meloxicam, and at very high pH values the effect of the increased solubility levels out. The free meloxicam exhibits a substantial increase in solubility only at pH levels above 7. At pH 13 meloxicam and its salts no longer exhibit any substantial differences in solubility. Accordingly, elevated dissolution rates can theoretically be expected for meloxicam salts at pH values above 4, and for free meloxicam only at pH values above 7.

It is known that the pH value of gastric juices can vary between 1 and 6 in fasting patients and is usually between 3 and 5 in non-fasting patients.

Since meloxicam salts with bases in the acidic pH range which prevails in the stomach have very low solubility, one might expect that a solid meloxicam salt in this environment would dissolve only very slowly and thus be available for resorption or that a corresponding meloxicam salt already dissolved would be precipitated in this environment. An essential difference in resorption characteristics would not be expected between meloxicam and its salts under these conditions on the basis of the solubility data. On the other hand, one would expect salts of meloxicam with bases in a less acidic medium of the small intestine to dissolve faster and to a greater degree than free meloxicam and be absorbed there correspondingly faster than the free meloxicam. The release and resorption of the active substance only in the small intestine, whilst the active substance might be protected by a gastric juice-resistant coating during its passage through the stomach, is not however suitable as a solution to the problem of the invention. The passage through the stomach after a pharmaceutical preparation has been administered takes too long, with the result that acute pain is not treated rapidly enough. Moreover, the time taken for the effect to set in would depend to a considerable extent on what had been eaten and would thus be subject to individual fluctuations.

When choosing a suitable form of active substance for developing a formulation capable of solving the problem of the invention, it is necessary to take account not only of the pH-dependent solubilities but also other physicochemical properties of meloxicam and its salts. Polymorphism of the active component, possibly the presence of various crystalline, variously solvated or amorphous modifications, can have a considerable influence on the chemical, biological and pharmaceutical properties of a drug. The meloxicam meglumin salt shows a strong tendency to form various polymorphic forms and crystallises out of various organic solvents, e.g. acetone, methanol, ethanol, ethanol/water (8:2, v/v) and isopropanol, in various crystalline modifications which contain 4–5% water of hydration, as can be shown by microscopic, IR-spectroscopic and thermal analysis as well as X-ray powder diffractometry. FIG. 1 shows an overview of the polymorphism present. Moreover, the meloxicam-meglumin salt displays only a slight tendency to spontaneous crystallisation.

The crystalline monohydrate modification of the meloxicam-meglumin salt is hygroscopic, whereas the meloxicam-sodium salt has no hygroscopic properties. Under ambient conditions the monohydrate of the meloxicam-meglumin salt is the stable modification, but at a relative humidity of over 75% a dihydrate is formed. The enclosed water can only be eliminated from the dihydrate under conditions of very great dryness. However, after dehydration, no stable anhydrous modification is obtained, but the anhydrous form very rapidly absorbs water to form the monohydrate form which is stable under ambient conditions. The water absorption/desorption characteristics of meloxicam-meglumin exhibit a hysteresis effect. By intensive drying over a fairly long period the anhydrous form changes more and more into an amorphous form and after 24 h at 100° C. the material is totally amorphous.

In particular, the polymorphism and hygroscopic nature of the meloxicam-meglumin salt led us to expect considerable problems for the use of this form of active substance in a pharmaceutical formulation, as only a uniform, stable modification capable of being manufactured reproducibly can be used.

The meloxicam-meglumin salt which is primarily obtained according to Example 3 of EP-A-0 002 482 is anhydrous and amorphous (drying at 80° over phosphorus pentoxide). This modification is certainly suitable for the preparation of parenteral formulations but not for the preparation of solid pharmaceutical preparations as this form does not satisfy the criteria specified above, but changes into a hydrated form when stored under normal ambient conditions.

Surprisingly, it has been found that meloxicam from the salts formed with bases becomes available for absorption substantially faster after adimninistration and in greater quantities than neutral meloxicam in spite of the low solubility at low pH levels which correspond to the environment of the stomach. The rise in the plasma levels after oral administration of the salts of meloxicam takes place considerably faster than when pure meloxicam is used. The high degree and rapidity of the rise in plasma levels which can be achieved with meloxicam salts, particularly the meloxicam-meglumin salt, could not have been expected by anyone skilled in the art, taking into account the properties of the NSAID salts known from the prior art. The increased solubility obtained by using a meloxicam salt surprisingly occurs in vivo even at low pH values. This makes it possible for large amounts of the active substance to be dissolved even immediately after administration and thus become available for absorption by the body.

Figure 4:
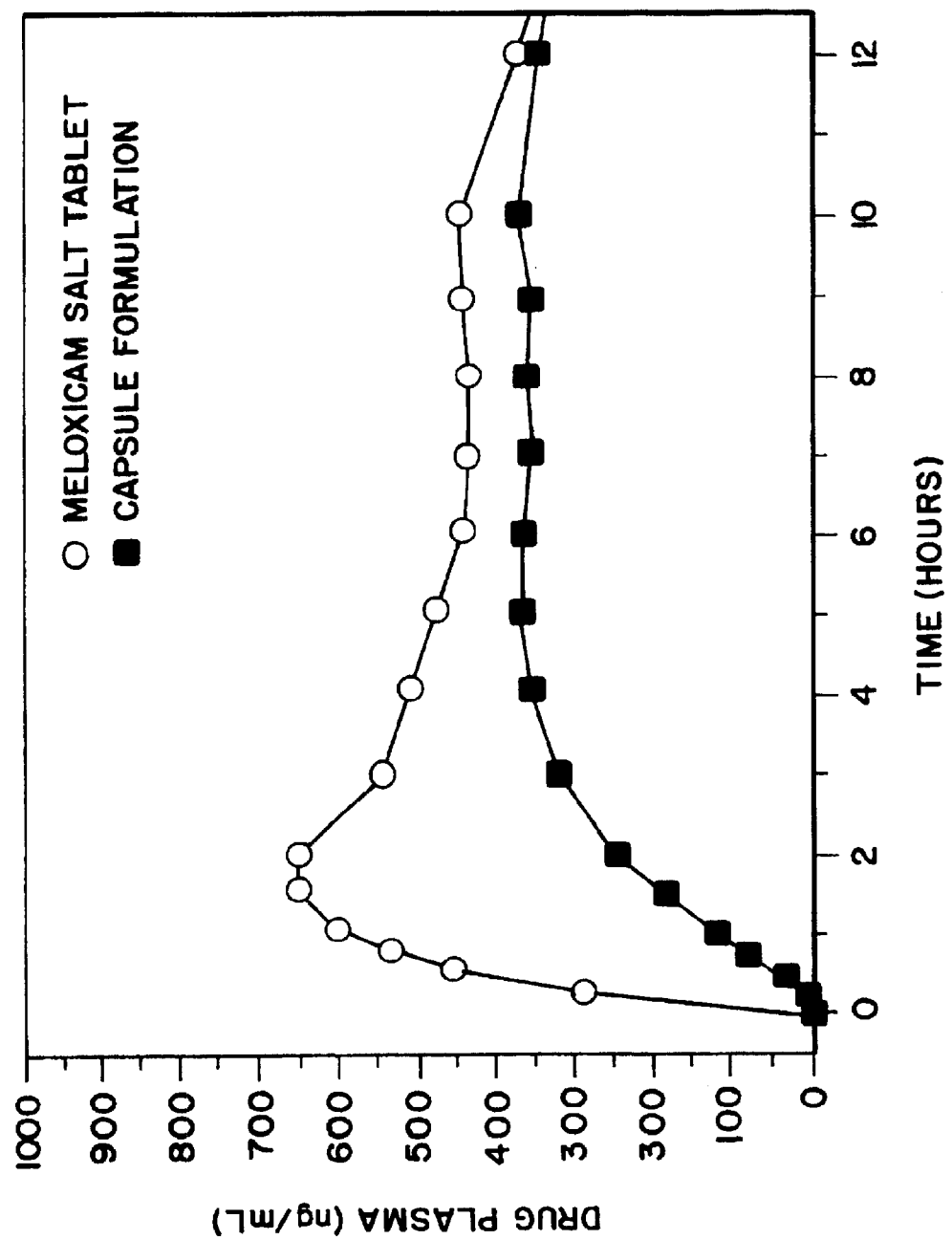

Example 7 together with FIG. 4 shows that after oral administration of a meloxicam salt formulation the plasma level rises considerably faster than after the administration of a conventional capsule formulation of the neutral active substance. Just 15 min after administration of the meloxicam-meglumin salt formulation according to the invention, a plasma level of 286 ng/ml is achieved, which virtually corresponds to the minimum plasma concentration in the steady-state, whilst 30 min after administration of the comparative formulation, still no appreciable plasma level (42 ng/ml) can be detected. Moreover, with the formulation according to the invention, after barely 2 hours a maximum plasma level of 812 ng/ml is obtained, which is twice as great as the minimum steady-state plasma level achieved with the comparative formulation (the maximum plasma level was determined on the basis of variability in time, not from the average curve in FIG. 4, but from the underlying individual curves). Thus, a rapid onset of activity as well as a particularly high activity can be expected in the first 2–3 hours after taking a formulation according to the invention, particularly a meloxicam-meglumin salt formulation, which is important for relieving acute pain. With the comparative formulation, on the other hand, no marked plasma level peak is achieved, but rather the plasma level rises more or less continuously until it reaches a plateau in the steady state.

The AUC0-∞ (AUC: area under the plasma concentration-time curve, 0-∞: from time 0 of the administration to infinity; measurement of resorption) of the conventional capsule formulation according to FIG. 4 is 14.1 μg h/mL, that of the meloxicam-meglumin salt formulation is 15.0 μg h/mL; the two are to be regarded as equivalent with regard to this parameter.

Other approaches to solving the problem of the present invention, e.g. the formation of inclusion compounds of meloxicam with β-cyclodextrin, did not produce sufficiently high plasma concentrations within a short period. Similarly, compression of a mixture of the two individual components meloxicam and meglumin did not solve the problem of the present invention.

The invention therefore relates to the use of a meloxicam salt of an inorganic or organic base for preparing an orally administered solid drug preparation from which the active substance is rapidly released and absorbed, for pain therapy, particularly for treating acute rheumatic attacks and for fighting acute pain. Suitable salts include, for example, the sodium, potassium or ammonium salt, the meglumin salt, the Tris salt or the salt of a basic amino acid such as L-lysine or L-arginine. The meloxicam-meglumin salt and the meloxicam sodium salt are preferred, the meloxicam-meglumin salt is particularly preferred, e.g. the meloxicam-meglumin salt dihydrate or especially the meloxicam-meglumin salt monohydrate.

In order to ensure rapid release of active substance after oral administration, it is also advantageous if the pharmaceutical preparation has a very short decomposition time, since as a rule the release of active substance can only proceed to a greater extent after breakdown. It has been found that a sufficiently short breakdown time can be achieved if the active substance is made into tablets directly with suitable excipients such as lactose, dicalcium phosphate, cellulose and suitable breakdown adjuvants such as crosslinked polyvinylpyrrolidone or sodium starch, i.e. the corresponding powder mixtures are compressed directly into tablets without any intermediate granulation of the powder before compression, as would normally be carried out. This has the advantage of being a simpler and cheaper method of production.

The invention thus also relates to an orally administered, solid pharmaceutical form of meloxicam from which the active substance is rapidly released and absorbed, for the treatment of pain, particularly for treating acute rheumatic attacks and for relieving acute pain, characterised in that meloxicam is present in the form of a salt with an inorganic or organic base, optionally together with conventional excipients and/or carriers, in a rapidly decomposing tablet produced by direct tabletting.

Suitable salts with an inorganic base include for example the sodium, potassium or ammonium salt of meloxicam. Examples of salts with organic bases include the meglumin salt, the Tris salt or a salt of meloxicam with a basic amino acid such as L-lysine or L-arginine. Salts which have proved particularly advantageous for the purposes of the present invention are the meglumin and sodium salt of meloxicam, the meloxicam-meglumin salt being particularly preferred, e.g. the meloxicam-meglumin salt dihydrate or more particularly the meloxicam-meglumin salt monohydrate.

Examples of excipients or carriers include microcrystalline cellulose, lactose, crosslinked polyvinylpyrrolidone, magnesium stearate, dicalcium phosphate and various starches.

Thirdly, the invention relates to a process for preparing an orally administered solid pharmaceutical preparation of meloxicam, which has a short decomposition time and from which the active substance is released and absorbed rapidly, for pain therapy, particularly for treating acute rheumatic attacks and for relieving acute pain, characterised in that an optionally pulverised meloxicam salt of an inorganic or organic base is intimately mixed with suitable pulverised excipients and/or carriers and compressed directly into tablets with no granulation of the powder before the compressing. The abovementioned meloxicam salts might be used, for example, the meglumin and the sodium salt of meloxicam being preferred. The meloxicam-meglumin salt is particularly preferred, for example the meloxicam-meglumin salt dihydrate or more particularly the meloxicam-meglumin salt monohydrate.

As already mentioned hereinbefore, the polymorphism and hygroscopy of the meloxicam-meglumin salt particularly led one to expect considerable difficulties in using the active substance in this form to achieve the objective of the invention, since only a reproducibly manufactured, uniform and stable modification can be used in a pharmaceutical formulation. Surprisingly, this condition can be met with the meloxicam-meglumin salt if, during crystallisation of the salt from a mixture of a water-miscible organic solvent and water, seed crystals consisting of crystalline meloxicam-meglumin salt monohydrate, preferably seed crystals of a meloxicam-meglumin salt monohydrate form previously crystallised from acetone/water, are added to the mixture. A product is then obtained, reproducibly and uniformly, which corresponds to the crystalline form of the seed crystals used.

From the crystalline meloxicam-meglumin salt monohydrate thus obtained, the crystalline meloxicam-meglumin salt dihydrate can be obtained by treating the monohydrate at high humidity.

Figure 2:
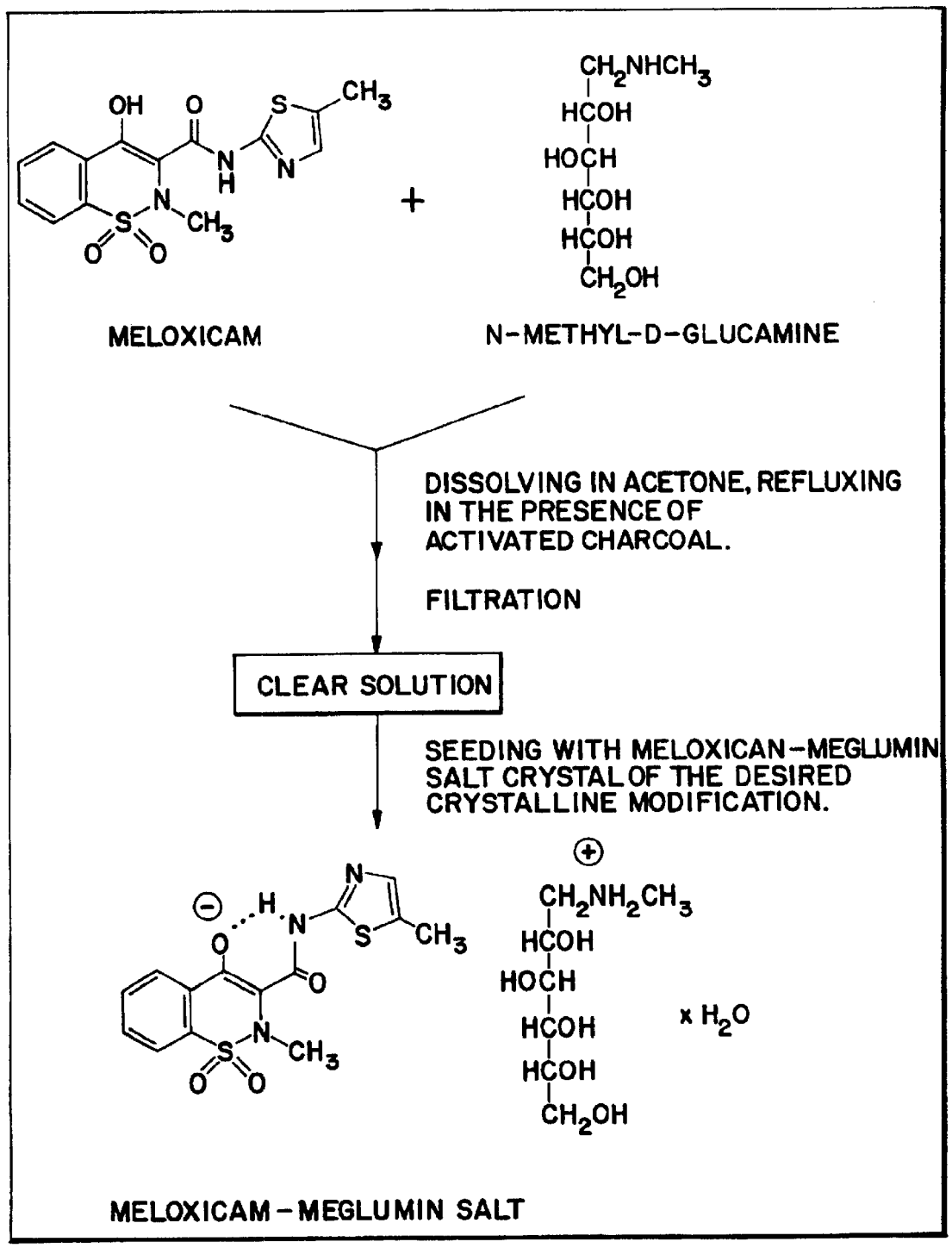

As a result of the slight tendency to spontaneous crystallisation and the strong tendency to form different polymorphic forms it is advisable to seed the solution with crystals of the desired monohydrate form in the last step of the production of the solid meloxicam-meglumin salt for pharmaceutical use. If desired, the dihydrate form can then be obtained from the monohydrate form as mentioned above. The synthesis plan is shown in FIG. 2.

Fourthly, the invention thus relates to the crystalline meloxicam-meglumin salt monohydrate, a process for preparing it, wherein meloxicam and meglumin are heated in a mixture of a water-miscible organic solvent and water and meloxicam-meglumin salt monohydrate seed crystals are added to the mixture for crystallisation, and an orally administered, solid pharmaceutical preparation containing meloxicam in the form of the crystalline meloxicam-meglumin salt monohydrate.

Examples of organic solvents include acetone, methanol, ethanol, n-propanol, i-propanol, tetrahydrofuran or dioxane, preferably acetone, ethanol, tetrahydrofuran and dioxane. Acetone and ethanol are particularly preferred, especially acetone.

In the mixture, organic solvent and water may be used in a ratio by volume of 10:1 to 100:1, preferably in a ratio of 20:1 to 50:1 or most preferably in a ratio of 35:1 to 45:1, a ratio of about 40:1 being particularly suitable when acetone is used.

Meloxicam and meglumin may for example be used in a molar ratio of 1:1.5 to 1.5:1, preferably in a molar ratio of 1:1.2 to 1.2:1, but particularly in an equimolar ratio.

Appropriately, the mixture may be heated with the addition of activated charcoal which is removed again before the addition of the seed crystals.

The amount of seed crystals added depends on the solvent system used and the quantity of mixture. For example, to a batch A=12.5 kg meloxicam, mixture B=5 to 50 g of meloxicam-meglumin salt monohydrate seed crystals (ratio by weight of A:B=125:0.05–0.5) are added, whilst if the solvent acetone/water is used the amount added is from 5 to 30 g, but particularly with a ratio of acetone: water=40:1 it is particularly appropriate to add 10 to 15 g of seed crystals. It is readily possible for the skilled man to determine the proper quantity of seed crystals for a given batch size and a given solvent system.

After the addition of the seed crystals the mixture is cooled to 10 to 30° C., but preferably to a temperature of about 20° C. Preferably, the mixture is then refluxed again and then slowly cooled to a temperature 10 and 30° C., preferably 15 to 25° C., but most usefully about 20° C. A fine crystalline crystal suspension of the desired meloxicam-meglumin salt monohydrate is obtained which is worked up in the usual way. The powder X-ray reflexes of the particularly preferred meloxicam meglumin salt monohydrate modification are contained in Table 2 which follows.

A fifth object of the invention is crystalline meloxicam-meglumin salt dihydrate, a process for preparing it, in which crystalline meloxicam-meglumin salt monohydrate is treated at high humidity, and an orally administered, solid pharmaceutical form containing meloxicam in the form of the crystalline meloxicam-meglumin salt dihydrate.

The treatment is carried out by storage for at least one day, preferably at least five days, at a high relative humidity. The relative humidity should be at least 75%, preferably at least 85%. The powder X-ray reflexes of the particularly preferred meloxicam meglumin salt dihydrate modification are shown in Table 3 which follows.

A sixth object of the invention is a process for preparing an orally administered solid pharmaceutical preparation containing meloxicam in the form of the meloxicam-meglumin salt monohydrate, which has a short decomposition time and from which the active substance is rapidly released and absorbed, for pain therapy, particularly for treating acute rheumatic attacks and for relieving acute pain, in which meloxicam and meglumin are heated in a mixture of a water-miscible organic solvent and water, meloxicam-meglumin salt monohydrate seed crystals are added to the mixture for crystallisation, then crystalline meloxicam-meglumin salt monohydrate is isolated in the usual way and powdered if desired and subsequently the meloxicam-meglumin salt monohydrate is intimately mixed with suitable powdered excipients and/or carriers and compressed directly into tablets with no granulation of the powder.

A seventh object of the invention is a process for preparing an orally administered solid pharmaceutical preparation containing meloxicam in the form of the meloxicam-meglumin salt dihydrate, which has a short decomposition time and from which the active substance is rapidly released and absorbed, for pain therapy, particularly for treating acute rheumatic attacks and for relieving acute pain, in which crystalline meloxicam-meglumin salt monohydrate is treated at high relative humidity, the meloxicam-meglumin salt dihydrate thus obtained is powdered, if desired, and then intimately mixed with suitable powdered excipients and/or carriers and compressed directly into tablets without granulation of the powder.

The following Examples are intended to illustrate the invention more fully:

EXAMPLE 1

Meloxicam Meglumin Salt Monohydrate 12.5 kg (35.57 mol) meloxicam and 6.9 kg (35.57 mol) meglumin are added successively, with stirring, to a mixture of 275 1 of acetone and 7:1 of water in a suitable reactor 1, then 1 kg of industrial-grade activated charcoal are added. The reaction mixture is heated and refluxed for 30 minutes. Then the mixture is forced through a pressure filter into a second reactor II. Reactor I and the pressure filter are washed out with 101 of acetone. The mixture is combined with 10–15 g meloxicam meglumin salt monohydrate seed crystals, cooled to 20° C. and stirred for 2 hours at this temperature. Then the mixture is heated, refluxed for 15 minutes and then slowly cooled to 20° C., during which time a fine crystalline crystal suspension is formed. This is stirred for 15 hours at 20° C. The crystal suspension is then centrifuged and subsequently spun dry. The centrifugal pellet is washed with 351 of acetone and again spun dry. The product is dried in the drying cupboard at 20–35° C. with fresh air for about 24 hours. Yield: 90.1% of theory; pale yellow crystalline powder, needle-like crystals; melting point: 120° C.

The crystalline meloxicam meglumin salt monohydrate thus obtained was investigated by IR-spectroscopy, by X-Ray Powder Diffraction and by thermal analysis (Thermogravimetry=TG; Differential Scanning Calorimetry=DSC).

1.1 IR Spectroscopy

Apparatus: Nicolet FTIR Spectrometer Magna—IR 550

Software: Nicolet Software Packet OMNIC, Version 1.20

Technique: Transmittance, KBr pellets (2.5 $\mu$mol substance/300 mg KBr), N2 rinse (flow: 151 N2/min)

Figure 5:
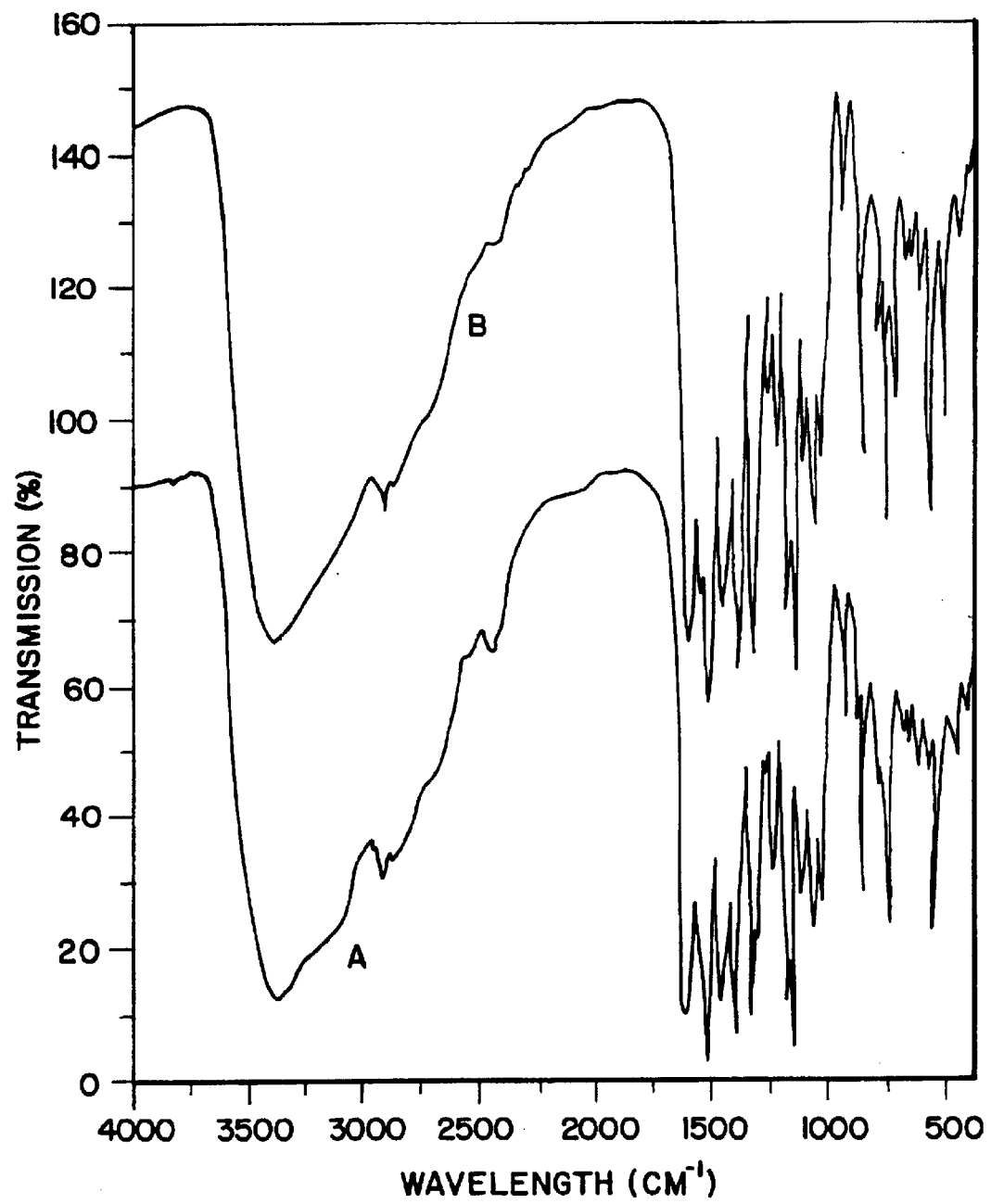

The FTIR spectrum is shown in FIG. 5. Compared with the FTIR spectrum of the dihydrate form there is a significant difference in the cleaved band at about 1300 cm$^{-1}$ in the spectrum of the monohydrate form, otherwise the spectra are very similar.

1.2 X-ray Powder Diffraction

Apparatus: Philips X-Ray Powder Diffractometer, CuK$_\alpha$radiation, $\alpha$=1.5418 Å, 35 mA, 35 kV Software: Software package GUFI 4.06 for data interpretation, Software package ORIGIN for data presentation Parameters: Range: 3–50° 2Θ Step scan: 0.01° 2Θ step width, 2 sec counting time for each step

TABLE 2

Powder X-Ray Reflexes and their intensities
(standardised), meloxicam meglumin salt monohydrate

| $2\Theta_{exp}$ [ ° ] | $d_{exp}$ [Å] | Intensity $I/I_o$ |
|---|---|---|
| 6.50 | 13.6 | 32 |
| 11.26 | 7.85 | 9 |
| 13.03 | 6.79 | 78 |
| 13.42 | 6.59 | 61 |
| 14.92 | 5.93 | 90 |
| 15.91 | 5.57 | 10 |
| 16.66 | 5.32 | 7 |
| 17.84 | 4.97 | 20 |
| 18.38 | 4.82 | 20 |
| 18.58 | 4.77 | 47 |
| 19.24 | 4.61 | 25 |
| 20.29 | 4.37 | 5 |
| 20.47 | 4.34 | 16 |
| 21.97 | 4.04 | 13 |
| 22.72 | 3.91 | 3 |
| 23.18 | 3.84 | 7 |
| 23.34 | 3.81 | 4 |
| 23.49 | 3.78 | 4 |
| 23.79 | 3.74 | 8 |
| 23.97 | 3.71 | 6 |
| 25.45 | 3.50 | 13 |
| 25.83 | 3.45 | 100 |
| 26.30 | 3.39 | 14 |
| 26.95 | 3.31 | 6 |
| 27.25 | 3.27 | 4 |
| 27.89 | 3.20 | 3 |
| 28.55 | 3.12 | 3 |
| 29.09 | 3.07 | 7 |
| 29.53 | 3.02 | 10 |
| 30.18 | 2.96 | 8 |
| 31.19 | 2.87 | 4 |
| 36.01 | 2.49 | 9 |
| 36.16 | 2.48 | 8 |
| 37.73 | 2.38 | 8 |
| 38.64 | 2.33 | 6 |
| 39.78 | 2.26 | 8 |

Figure 6:
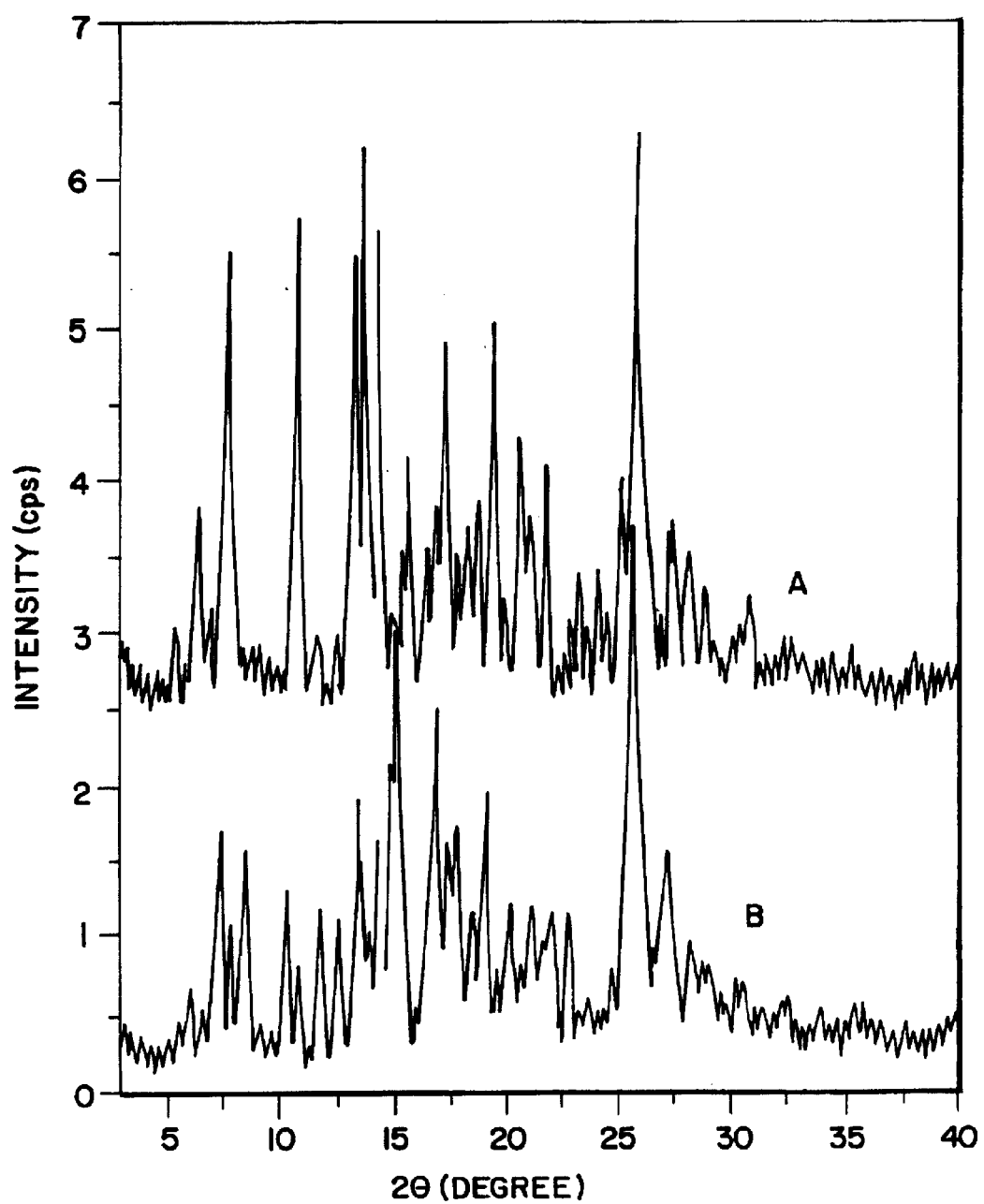

The X-ray powder diffraction pattern is shown in FIG. 6.

1.3 Thermal Analysis

TG: Apparatus' Mettler Microbalance M3, Temperature-controller TC15

Software: Mettler Software package STAR

Technique: (—$Al_2O_3$ melting pot, heating rate: 10 K/min, N2 atmosphere

DSC: Apparatus: Mettler DSC-20, temperature controller TC15

Software: Mettler Software package STAR

Technique: open Al melting pot, heating rate: 3 and 10 K/min, N2 atmosphere

A clear correlation can be found between the endothermic peak observed in the DSC diagram and the dehydration or melting processes. Dehydration and melting are clearly separate processes.

Figure 8:
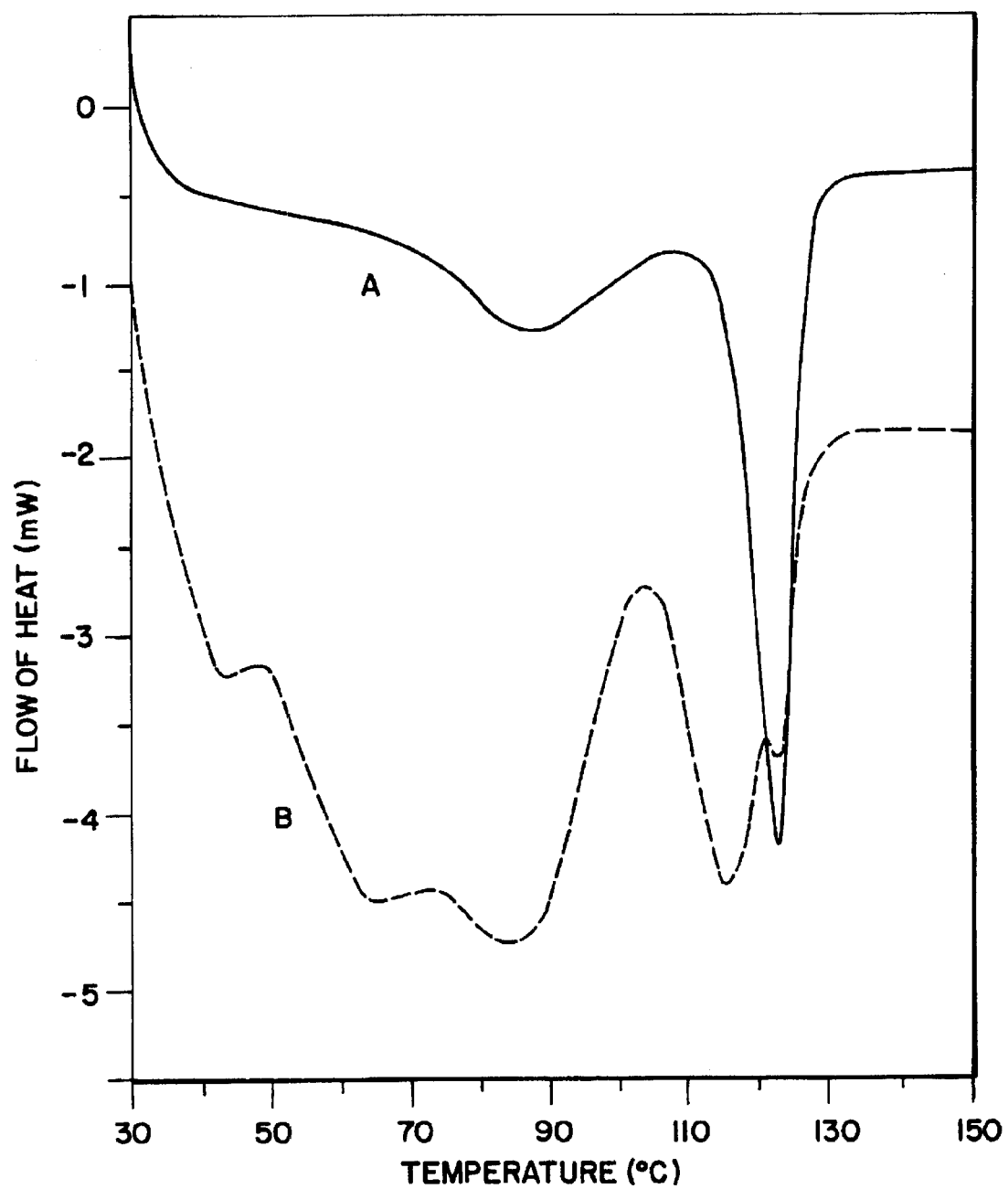

The DSC diagram is shown in FIG. 8.

EXAMPLE 2

Meloxicam Meglumin Salt Dihydrate

Crystalline meloxicam meglumin salt dihydrate is obtained by storing the crystalline meloxicam meglumin salt monohydrate obtained in Example 1 for five days over saturated potassium chloride solution at a relative humidity of 86% and a temperature of 20° C.

The crystalline meloxicam meglumin salt dihydrate thus obtained was investigated by IR-spectroscopy, by X-Ray Powder Diffraction and by thermal analysis (thermogravimetry=TG; Differential Scanning Calorimetry=DSC). The apparatus, software and parameters mentioned in Example 1 were used.

2.1 IR Spectroscopy: The FTIR Spectrum is Shown in FIG. 5.

2.2 X-Ray Powder Diffraction:

TABLE 3

Powder X-Ray Reflexes and their intensities
(standardised), meloxicam meglumin salt dihydrate

| $2\Theta_{exp}$ [ ° ] | $d_{exp}$ [Å] | Intensity $I/I_o$ |
|---|---|---|
| 5.99 | 14.8 | 13 |
| 6.95 | 12.7 | 13 |
| 7.36 | 12.0 | 41 |
| 7.82 | 11.3 | 22 |
| 8.25 | 10.7 | 18 |
| 8.47 | 10.4 | 38 |
| 10.32 | 8.6 | 32 |
| 10.85 | 8.2 | 18 |
| 11.86 | 7.46 | 29 |
| 12.61 | 7.01 | 26 |
| 13.46 | 6.58 | 49 |
| 13.81 | 6.41 | 19 |
| 14.29 | 6.20 | 37 |
| 14.48 | 6.11 | 42 |
| 14.97 | 5.92 | 53 |
| 15.28 | 5.80 | 96 |
| 16.88 | 5.25 | 65 |
| 17.39 | 5.10 | 39 |
| 17.78 | 4.99 | 42 |
| 18.41 | 4.81 | 25 |
| 19.08 | 4.65 | 50 |
| 19.55 | 4.54 | 14 |
| 20.10 | 4.41 | 28 |
| 21.12 | 4.20 | 24 |
| 21.70 | 4.09 | 19 |
| 21.95 | 4.05 | 25 |
| 22.80 | 3.90 | 26 |
| 25.65 | 3.47 | 100 |
| 26.02 | 3.42 | 43 |
| 27.04 | 3.30 | 35 |
| 27.37 | 3.26 | 26 |
| 28.29 | 3.15 | 19 |
| 28.92 | 3.09 | 14 |
| 30.43 | 2.94 | 13 |

The X-ray powder diffraction pattern is shown in FIG. 6.

2.3 Thermal Analysis

Clear correlation of the endothermic peak observed in the DSC diagram is not possible since dehydration and melting processes overlap.

Figure 9:
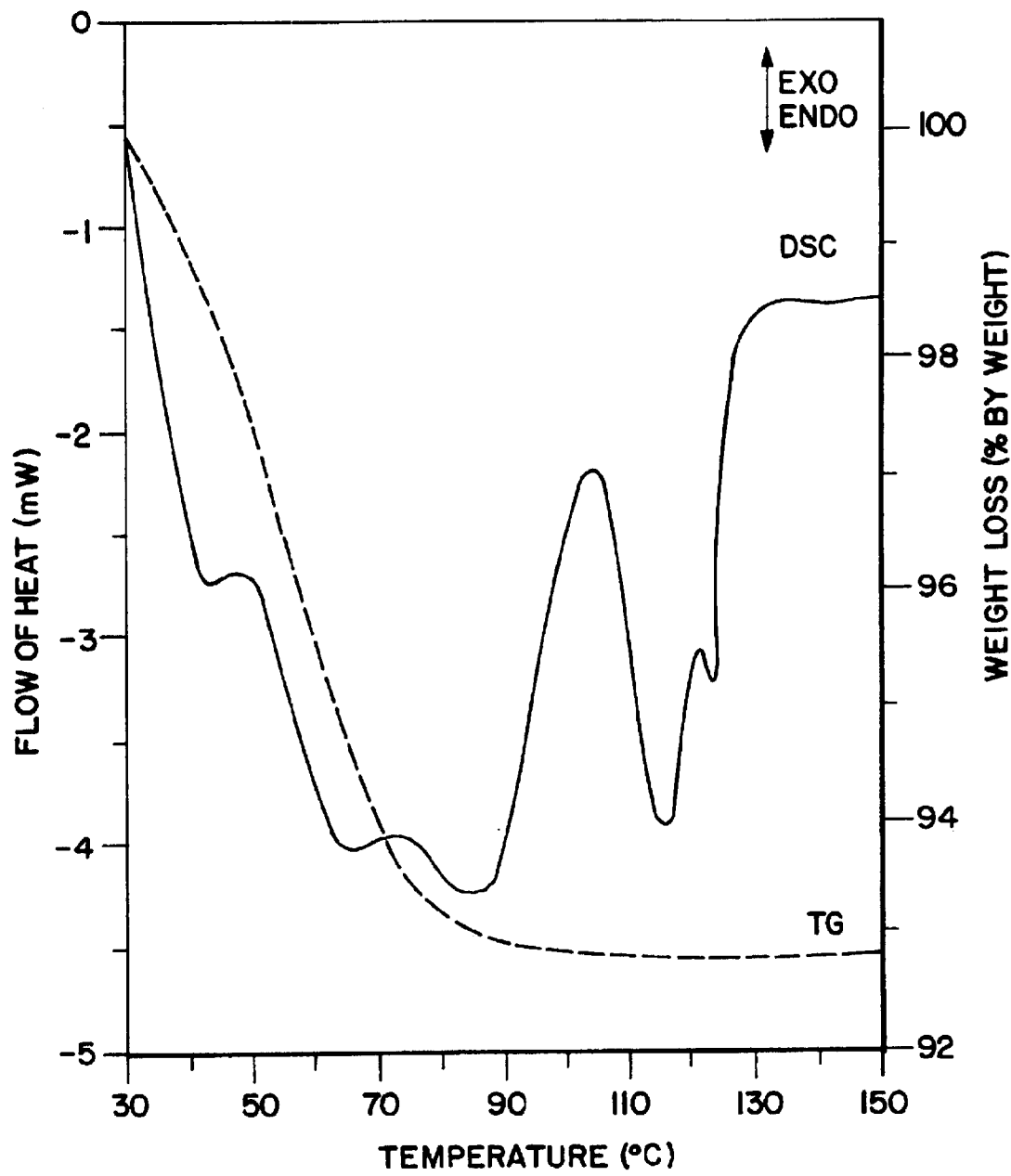

The TG/DSC diagrams obtained are shown in FIGS. 8 and 9.

The DSC diagram of the dihydrate form is very characteristic with a broad and structured endothermic peak between ambient temperature and 130° C. Five clear minima are visible at about 45, 65, 85, 115 and 125° C. The comparison with the DSC diagram of the monohydrate form in FIG. 8 clearly shows the differences between these two hydrate forms. All they have in common s the endothermic peaks at about 85–90° C. (dehydration step) and at about 125° C. (melting process).

EXAMPLE 3

Anhydrous Meloxicam Meglumin Salt

Figure 7:
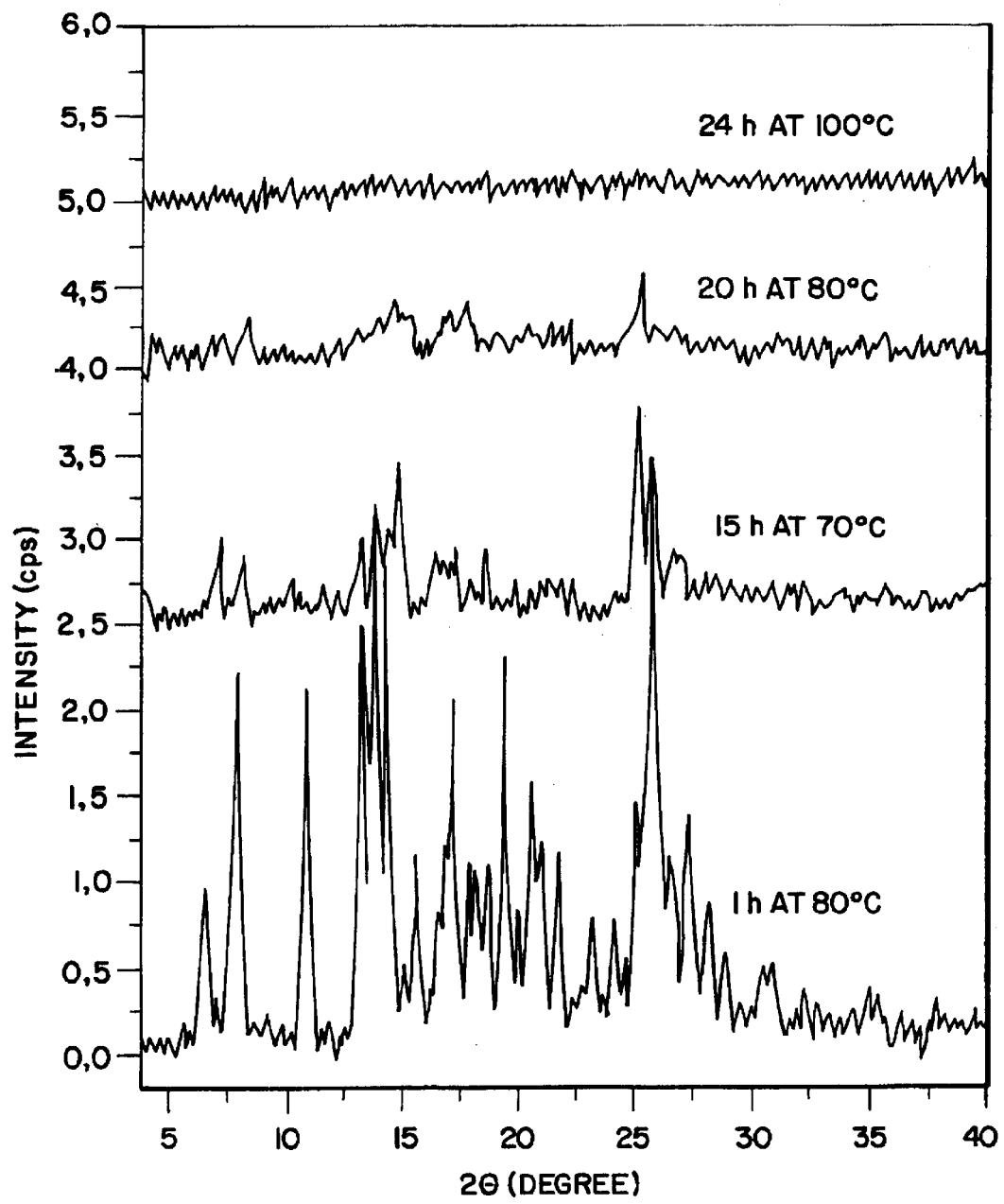

Meloxicam meglumin salt monohydrate can be converted into an anhydrous form by dehydration. The relevant parameters of the dehydration process are the temperature and duration of dehydration, the influence of which were observed by X-ray powder diffraction. The longer the dehydration process lasts, the less crystalline is the resulting material. After 24 hours at 100° C. the meloxicam meglumin salt is anhydrous and totally amorphous, whereas after one hour at 80° C. no change can be detected in the monohydrate used. The X-ray powder diffraction diagrams obtained after 1 hour at 80° C., 15 hours at 70° C., 20 hours at 80° C. and 24 hours at 100° C. are shown in FIG. 7.

EXAMPLE 4

Meloxicam Meglumin Salt (Monohydrate) Tablets, Directly Compressed

| Recipe for meloxicam meglumin salt tablets: | |
|---|---|
| meloxicam meglumin salt calculated as meloxicam | 7.5 mg |
| microcrystalline cellulose | 205.5 mg |
| lactose | 205.5 mg |
| polyvinylpyrrolidone (crosslinked) | 22.5 mg |
| magnesium stearate | 4.5 mg |

Preparation:

The active substance (ground or not ground) is intimately mixed with the excipients specified in the recipe and compressed directly to form tablets.

EXAMPLE 5

Meloxicam Sodium Salt Tablets, Compressed Directly

| Recipe for meloxicam sodium salt tablets: | |
|---|---|
| meloxicam sodium salt calculated as meloxicam | 7.5 mg |
| microcrystalline cellulose | 209.5 mg |
| lactose | 205.5 mg |
| polyvinylpyrrolidone (crosslinked) | 22.5 mg |
| magnesium stearate | 4.5 mg |

Preparation:

The active substance (ground or not ground) is prepared for example according to the data in EP-A-0 002 482, is intimately mixed with the excipients specified in the recipe and compressed directly to form tablets.

Figure 3:
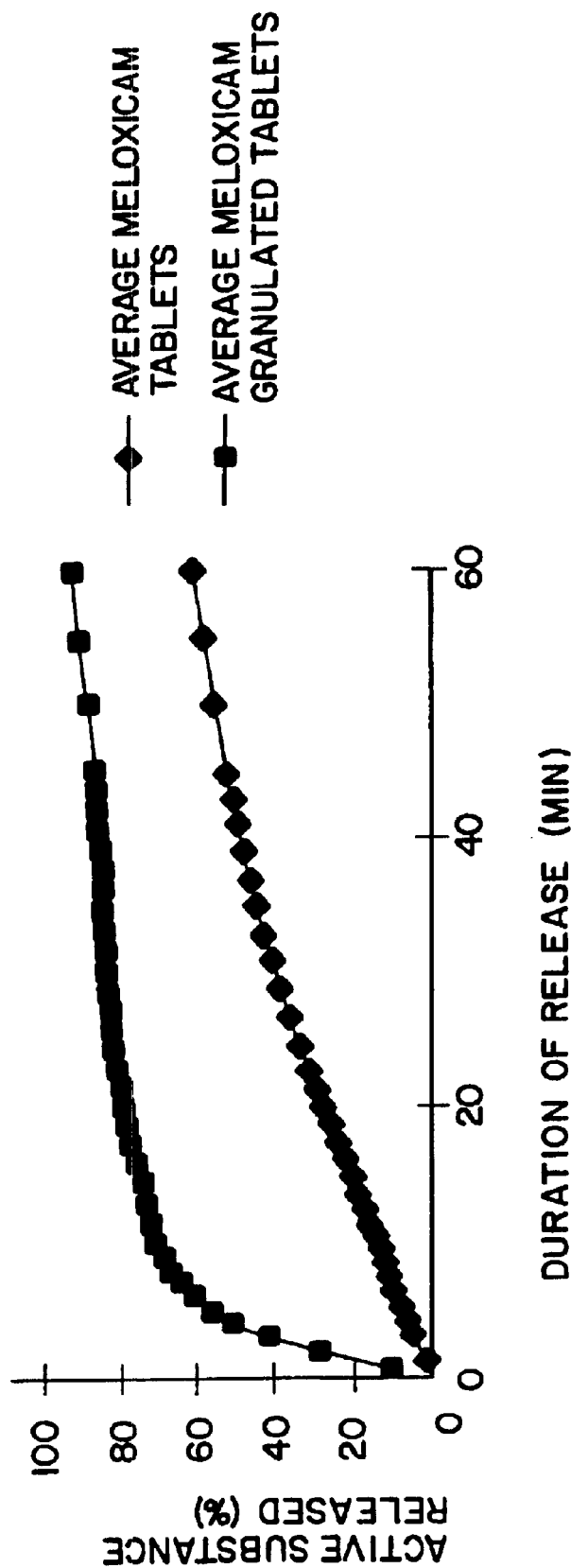

EXAMPLE 6 in Vitro Release:

Meloxicam (Neutral)/Directly Compressed Versus Meloxicam (Neutral)/Granulated/Compressed When the release profiles of two tablets are compared with each other, one formulation having been produced by compressing a powder mixture whilst the other has been prepared by compressing previously granulated powder, it is apparent that the meloxicam is released more quickly from the tablet prepared by compressing of the powder mixture (FIG. 3). The release was measured over the investigation period by spectral-photometric determination of the active substance at its extinction peak.

| Recipe for meloxicam tablets: (directly compressed from powder) | |
|---|---|
| meloxicam | 7.5 mg |
| microcrystalline cellulose | 210.0 mg |
| lactose | 205.0 mg |
| polyvinylpyrrolidone (crosslinked) | 22.5 mg |
| magnesium stearate | 4.5 mg |

| Recipe for meloxicam tablets: (compressed from granules) | |
|---|---|
| meloxicam | 7.5 mg |
| microcrystalline cellulose | 210.0 mg |
| lactose | 205.0 mg |
| polyvinylpyrrolidone (crosslinked) | 22.5 mg |
| magnesium stearate | 4.5 mg |

EXAMPLE 7

Human Trials for Verifying the Advantages of the Pharmaceutical Composition According to the Invention Over a Conventional Preparation The following formulations were tested on 18 test subjects in a single dose in a cross-over trial:

| Recipe for meloxicam meglumin salt tablets (directly compressed): | |
|---|---|
| meloxicam meglumin salt calculated as meloxicam | 7.5 mg |
| microcrystalline cellulose | 205.5 mg |
| lactose | 205.5 mg |
| polyvinylpyrrolidone (crosslinked) | 22.5 mg |
| magnesium stearate | 4.5 mg |

| Recipe for meloxicam (granulated) capsules: | |
|---|---|
| meloxicam | 7.5 mg |
| sodium citrate | 15.0 mg |
| microcrystalline cellulose | 102.0 mg |
| lactose | 23.5 mg |
| polyvinylpyrrolidone (soluble) | 10.5 mg |
| silicon dioxide (highly dispersed) | 3.5 mg |
| polyvinylpyrrolidone (crosslinked) | 16.3 mg |
| magnesium stearate | 1.7 mg |

FIG. 4 shows the averages of the plasma levels obtained. It is apparent that the differences found in the dissolution processes in vitro are also seen in the blood levels in humans after oral administration. When the rapidly released form with the salt of meloxicam was used, the plasma levels rose faster, leading to an increase in the maximum plasma levels and a shortening of the time taken to achieve these levels.

With an onset of activity correlated to the plasma level a formulation of this kind will give a faster acting analgesic effect.

What is claimed is:

1. Crystalline meloxicam meglumin salt monohydrate or crystalline meloxicam meglumin salt dihydrate.

2. A process for preparing crystalline meloxicam-meglumin salt monohydrate, the process comprising:

(a) heating meloxicam and meglumin in a solvent mixture of a water-miscible organic solvent and water; and (b) adding meloxicam-meglumin salt monohydrate seed crystals to the solvent mixture containing meloxicam and meglumin to obtain crystalline meloxicam-meglumin salt monohydrate.

3. The process of claim 2, wherein the water-miscible organic solvent is acetone, methanol, ethanol, n-propanol, isopropanol, tetrahydrofuran, or dioxane.

4. The process of claim 2, wherein the water-miscible organic solvent is acetone or ethanol.

5. The process of claim 2, wherein the mixture of organic solvent and water are used in a ratio by volume of 10:1 to 100:1.

6. The process of claim 2, wherein the meloxicam and meglumin are used in a molar ratio of 1:1.5 to 1.5:1.

7. The process of claim 2, wherein a mixture of:

(A) 12.5 kg meloxicam; and (B) 5 to 50 g of meloxicam-meglumin salt monohydrate seed crystals are added.

8. A process for preparing crystalline meloxicam-meglumin salt dihydrate, wherein crystalline meloxicam-meglumin salt monohydrate is treated at a relative humidity of at least 75%.

9. A process for preparing an orally administrable solid pharmaceutical preparation containing meloxicam in the form of the crystalline meloxicam-meglumin salt monohydrate, the process comprising:

(a) heating meloxicam and meglumin in a solvent mixture of a water-miscible organic solvent and water;

(b) adding meloxicam-meglumin salt monohydrate seed crystals to the solvent mixture containing meloxicam and meglumin to obtain crystalline meloxicam-meglumin salt monohydrate;

(c) separating crystalline meloxicam-meglumin salt monohydrate from the solvent mixture;

(d) optionally powdering the crystalline meloxicam-meglumin salt monohydrate and intimately mixing the crystalline meloxicam-meglumin salt monohydrate with a conventional powdered excipient or carrier to obtain a pharmaceutical mixture; and (e) compressing the pharmaceutical mixture from step (d) directly into tablets with no granulation of the powder.

10. A process for preparing an orally administrable solid pharmaceutical preparation containing meloxicam in the form of the meloxicam-meglumin salt dihydrate, wherein crystalline meloxicam-meglumin salt monohydrate is treated at a relative humidity of at least 75%, the meloxicam-meglumin salt dihydrate thus obtained is optionally powdered, and then intimately mixed with suitable powdered excipient carrier and compressed directly into tablets without granulation of the powder.

11. A solid pharmaceutical composition for oral administration comprising meloxicam in the form of the crystalline meloxicam meglumin salt monohydrate.

12. A solid pharmaceutical composition for oral administration comprising meloxicam in the form of the crystalline meloxicam meglumin salt dihydrate.

13. The process of claim 2, wherein a mixture of:

(A) meloxicam; and (B) meloxicam-meglumin salt monohydrate seed crystals are added in a corresponding ratio by weight of A:B of 125:0.05–0.5.

14. The process of claim 2, further comprising:

(c) separating crystalline meloxicam-meglumin salt monohydrate from the solvent mixture.

15. The composition in accordance with claim 11, further comprising a conventional powered carrier or excipient.

16. The composition in accordance with claim 12, further comprising a conventional powered carrier or excipient.

17. A method for the treatment of rheumatic diseases or acute pain, the method comprising orally administering a host suffering from rheumatic diseases or acute pain a therapeutic amount of composition in accordance with claim 11.

18. A method for the treatment of rheumatic diseases or acute pain, the method comprising orally administering a host suffering rheumatic diseases or acute pain a therapeutic amount of composition in accordance with claim 12.

* * * * *